(12) United States Patent
Kreindel

(10) Patent No.: US 8,579,896 B2
(45) Date of Patent: Nov. 12, 2013

(54) METHOD AND SYSTEM FOR INVASIVE SKIN TREATMENT

(75) Inventor: Michael Kreindel, Haifa (IL)

(73) Assignee: Syneron Medical, Inc. (IL)

( * ) Notice: Subject to any disclaimer, the term of this patent is extended or adjusted under 35 U.S.C. 154(b) by 288 days.

(21) Appl. No.: 12/876,765

(22) Filed: Sep. 7, 2010

(65) Prior Publication Data

US 2011/0196363 A1 Aug. 11, 2011

Related U.S. Application Data

(63) Continuation of application No. 12/702,723, filed on Feb. 9, 2010, and a continuation of application No. 12/702,647, filed on Feb. 9, 2010, each which is a continuation of application No. 10/931,271, filed on Sep. 1, 2004, now abandoned.

(51) Int. Cl.
*A61B 18/08* (2006.01)

(52) U.S. Cl.
USPC .......................................................... 606/49

(58) Field of Classification Search
USPC ................. 606/32, 40, 41; 607/99, 101–102
See application file for complete search history.

(56) References Cited

U.S. PATENT DOCUMENTS

| | | | | |
|---|---|---|---|---|
| 4,211,230 A * | 7/1980 | Woltosz | 606/40 |
| 4,532,924 A * | 8/1985 | Auth et al. | 606/50 |
| 4,550,728 A * | 11/1985 | Runyon et al. | 606/36 |
| 5,348,554 A * | 9/1994 | Imran et al. | 606/41 |
| 5,888,198 A * | 3/1999 | Eggers et al. | 604/114 |
| 6,053,172 A * | 4/2000 | Hovda et al. | 128/898 |
| 6,066,134 A * | 5/2000 | Eggers et al. | 606/32 |
| 6,231,571 B1 * | 5/2001 | Ellman et al. | 606/41 |
| 6,277,116 B1 * | 8/2001 | Utely et al. | 606/42 |
| 6,325,797 B1 * | 12/2001 | Stewart et al. | 606/41 |
| 6,413,255 B1 * | 7/2002 | Stern | 606/41 |
| 6,425,912 B1 * | 7/2002 | Knowlton | 607/101 |
| 6,482,204 B1 * | 11/2002 | Lax et al. | 606/42 |
| 6,743,211 B1 * | 6/2004 | Prausnitz et al. | 604/239 |
| 2002/0120260 A1 * | 8/2002 | Morris et al. | 606/41 |
| 2004/0181216 A1 * | 9/2004 | Kelly et al. | 606/41 |
| 2008/0183167 A1 * | 7/2008 | Britva et al. | 606/41 |
| 2009/0299361 A1 * | 12/2009 | Flyash et al. | 606/33 |

* cited by examiner

*Primary Examiner* — Michael Peffley
*Assistant Examiner* — Daniel Fowler
(74) *Attorney, Agent, or Firm* — Smith Risley Tempel Santos LLC; Gregory Scott Smith

(57) ABSTRACT

A system and method for simultaneously heating a plurality of discrete skin volumes to a coagulation temperature. The system comprises an applicator containing an electrode having a plurality of spaced apart protruding conducting elements configured to contact the skin surface at a plurality of discrete locations. A controller applies a voltage to the electrode so as to simultaneously heat a plurality of skin volumes to a coagulation temperature when the applicator is applied to the skin surface.

13 Claims, 3 Drawing Sheets

METHOD AND SYSTEM FOR INVASIVE SKIN TREATMENT

CROSS-REFERENCE TO RELATED APPLICATIONS

This application is being filed under 35 USC 111 and is a continuation of, and claims the benefit of the filing date of U.S. patent application Ser. Nos. 12/702,723 and 12/702,647, both of which were filed on Feb. 9, 2010 and both of which are continuations of and claim priority to U.S. patent application Ser. No. 10/931,271 that was filed on Sep. 1, 2004 and bears the title of METHOD AND SYSTEM FOR INVASIVE SKIN TREATMENT and which has now been abandoned.

FIELD OF THE INVENTION

The invention relates to methods and systems for skin treatment.

BACKGROUND OF THE INVENTION

Directed damage of the skin is used to stimulate regrowth of collagen and to improve skin appearance. A well known method of directed damage is ablating the epidermis using laser radiation having wavelengths strongly absorbed by water so as to heat the water to above boiling temperature. Typical lasers used for epidermis ablation are $CO_2$ and Er:YAG lasers. Ablating the epidermis using RF (radiofrequency) current is described in U.S. Pat. No. 6,309,387. This treatment significantly reduces wrinkles and improves the skin appearance. The main disadvantages of skin resurfacing are the long healing period that can be over a month long and the high risk of dischromia. These disadvantages have reduced the popularity of ablative skin resurfacing in recent years.

Non-ablative skin resurfacing is based on heating of the dermis to a sub-necrotic temperature with simultaneous cooling of the skin surface. U.S. Pat. No. 5,810,801 describes penetrating the dermis with infrared laser radiation with dynamic cooling of the skin surface using a cryogen spray.

Wrinkles are created in skin due to the breakage of collagen fibers and to the penetration of fat into the dermal structure. Thus, destroying adipose cells and structure, can improve the surface structure. However, most wrinkle treatment methods target the collagen and do not have a significant effect on deep wrinkles. Radio frequency (RF) energy has been used for the treatment of the epidermal and dermal layers of the skin. For example, U.S. Pat. No. 6,749,626 describes use of RF for collagen formation in dermis. This patent describes a method for collagen scar formation. U.S. Pat. Nos. 6,470,216, 6,438,424, 6,430,446, and 6,461,378 disclose methods and apparatuses for affecting the collagen matrix using RF with special electrode structures together with cooling and smoothing of the skin surface. U.S. Pat. Nos. 6,453,202, 6,405,090, 6,381,497, 6,311,090, 5,871,524, and 6,452,912 describe methods and apparatuses for delivering RF energy to the skin using a membrane structure. U.S. Pat. Nos. 6,453,202 and 6,425,912 describe methods and apparatuses for delivering RF energy and creating a reverse temperature gradient on the skin surface. Although a non-ablative treatment is much safer and does not scar the skin tissue, the results of non-ablative treatments are less satisfactory.

A method described in U.S. patent application No. 20030216719 attempts to maintain the efficiency of ablative treatment with a shorter healing time and a lower risk of adverse effects. The device described in that patent coagulates discrete regions of the skin where the regions have a diameter of tens of micrometers and the distance between the regions is larger than the regions themselves. This treatment provides skin healing within a few days but the results are very superficial and less spectacular than with $CO_2$ laser treatment, even after multiple treatments.

U.S. Pat. No. 6,277,116 describes a method of applying electromagnetic energy to the skin through an array of electrodes and delivery electrolyte using a microporous pad.

A device for ablation of the skin stratum corneum using RF electrodes is described in U.S. Pat. Nos. 6,711,435, 6,708,060, 6,611,706, and 6,597,946. However, the parameters of this device are optimized for the ablation of the stratum corneum so as to enhance drug penetration into the skin, and not for thermal collagen remodeling.

SUMMARY OF THE INVENTION

The present invention provides a system and method for simultaneously heating skin at a plurality of discrete regions of the skin. The invention may be used for collagen remodeling. In accordance with the invention RF energy is applied to the skin at a plurality of discrete locations on the skin. The RF energy is applied using an electrode having a plurality of spaced apart protruding conducting pins. When the electrode is applied to the skin surface, each protruding conducting pin contacts the skin surface at a different location, so that the plurality of pins contacts the skin at a plurality of discrete locations. An RF voltage is then applied to the electrode so as to generate an electric current in the skin that heats the skin to a coagulation temperature simultaneously at a plurality of discrete regions of the skin. Coagulation temperatures are typically in the range of about 60.degree. C. to about 70.degree. C.

The protruding pins may have blunt tips which do not penetrate into the skin when the electrode is applied to the skin. In this case, the discrete regions of treated skin are located at the skin surface in the epidermis. Alternatively, the pins may have sharp tips that allow the protruding pin to penetrate the skin into the dermis. In this way, the discrete regions of treated skin are located in the dermis.

In another embodiment, the protruding elements are provided with sharp tips that allow the elements to penetrate into the skin. After application of the RF current in the skin, the protruding elements are pressed into the skin and an electrical current is then generated that coagulates tissue in the vicinity of the tip of each protruding element. The mechanical properties of the skin are changed after coagulation and the protruding elements may penetrate inside the skin without excessive pressure. A pre-pulse of RF energy can be applied to the skin in order to soften the skin tissue so as to facilitate penetration of the protruding elements into the skin.

The surface of the skin may be pre-cooled and/or cooled during the treatment to avoid damage to the skin in the area between protruding elements. Skin cooling may be provided by contact cooling or by applying a pre-cooled liquid or cryogen spray.

The invention may be used in wrinkle treatment, collagen remodeling, skin tightening, loose skin treatment, sub-cutaneous fat treatment or skin resurfacing.

Thus in its first aspect, the invention provides a system for simultaneously heating a plurality of discrete skin volumes to a coagulation temperature, comprising:
(a) an applicator comprising an electrode having a plurality of spaced apart protruding conducting elements configured to contact the skin surface at a plurality of discrete locations; and (b) a controller configured to apply a voltage to the electrode so as to simultaneously heat a plurality of skin volumes to a coagulation temperature when the applicator is applied to the skin surface.

In its second aspect, the invention provides a method for simultaneously heating a plurality of discrete skin volumes to a coagulation temperature, comprising:
(a) applying an applicator to the skin surface, the applicator comprising an electrode having a plurality of spaced apart protruding conducting elements configured to contact the skin surface at a plurality of discrete locations; and
(b) applying a voltage to the electrode so as to simultaneously heat a plurality of skin volumes to a coagulation temperature.

In the case when protruding part of the electrode penetrates within the skin the size of protruding elements should be small enough to avoid significant damage of the skin surface. Preferable size of protruding elements is from 10 to 200 microns and coagulation depth can be varied from 100 microns up to 2 mm for invasive electrodes.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF PREFERRED EMBODIMENTS

Figure 1:
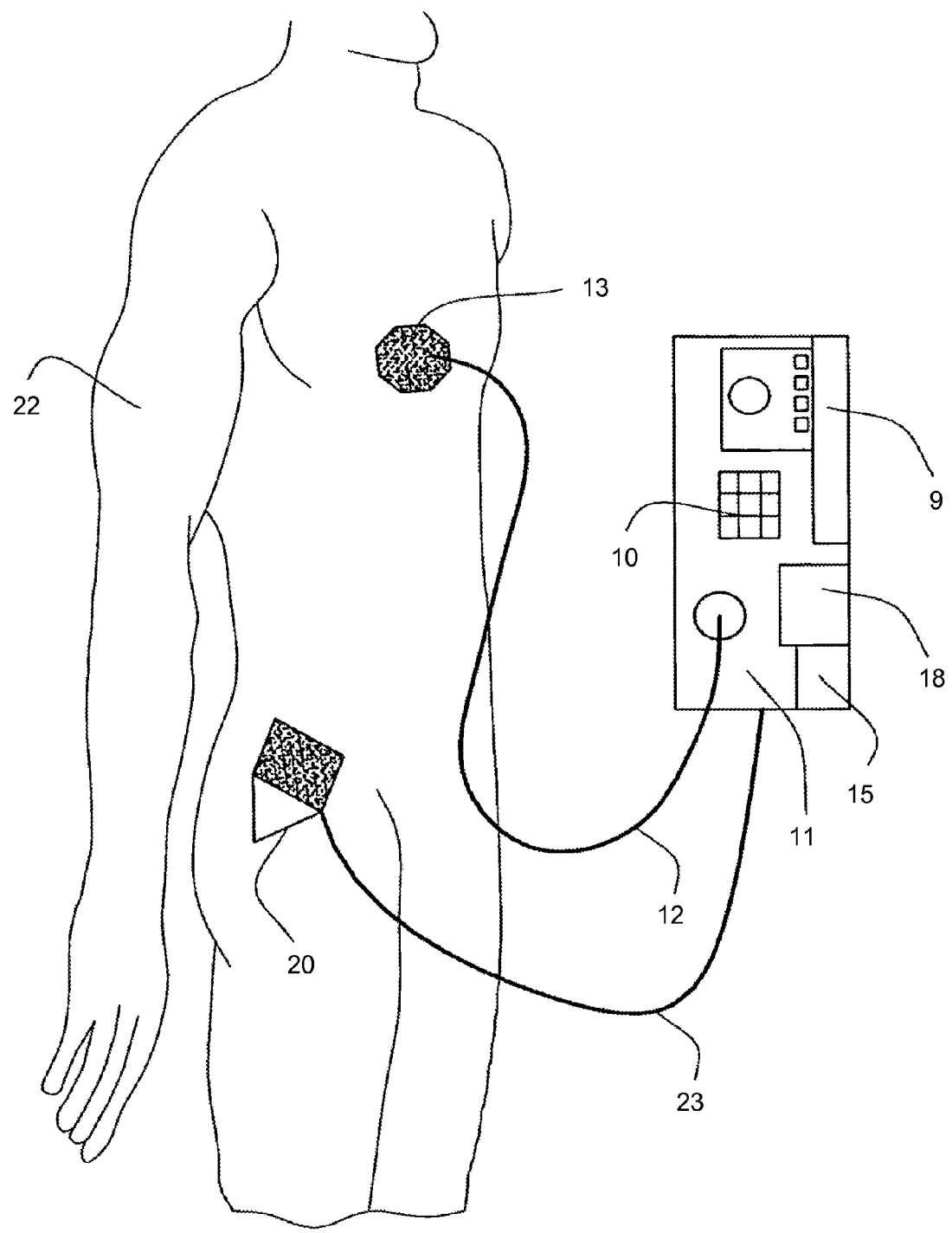
FIG. 1 shows a system for treating skin simultaneously at a plurality of discrete regions of skin, in accordance with the invention.

FIG. 1 shows a system for applying RF energy to a plurality of discrete regions of skin in accordance with the invention. The system includes an applicator 13, to be described in detail below, configured to apply RF energy simultaneously to a plurality of discrete regions of skin of an individual 22. The applicator 13 is connected to a control unit 11 via a cable 12. The control unit 11 includes a power source 18. The power source 18 is connected to an RF generator 15 that is connected to electrodes in the applicator 13 via wires in the cable 12. The control unit 11 has an input device such as a keypad 10 that allows an operator to input selected values of parameters of the treatment, such as the frequency, pulse duration and intensity of the RF energy. The control unit 11 optionally contains a processor 9 for monitoring and controlling various functions of the device.

Figure 2:
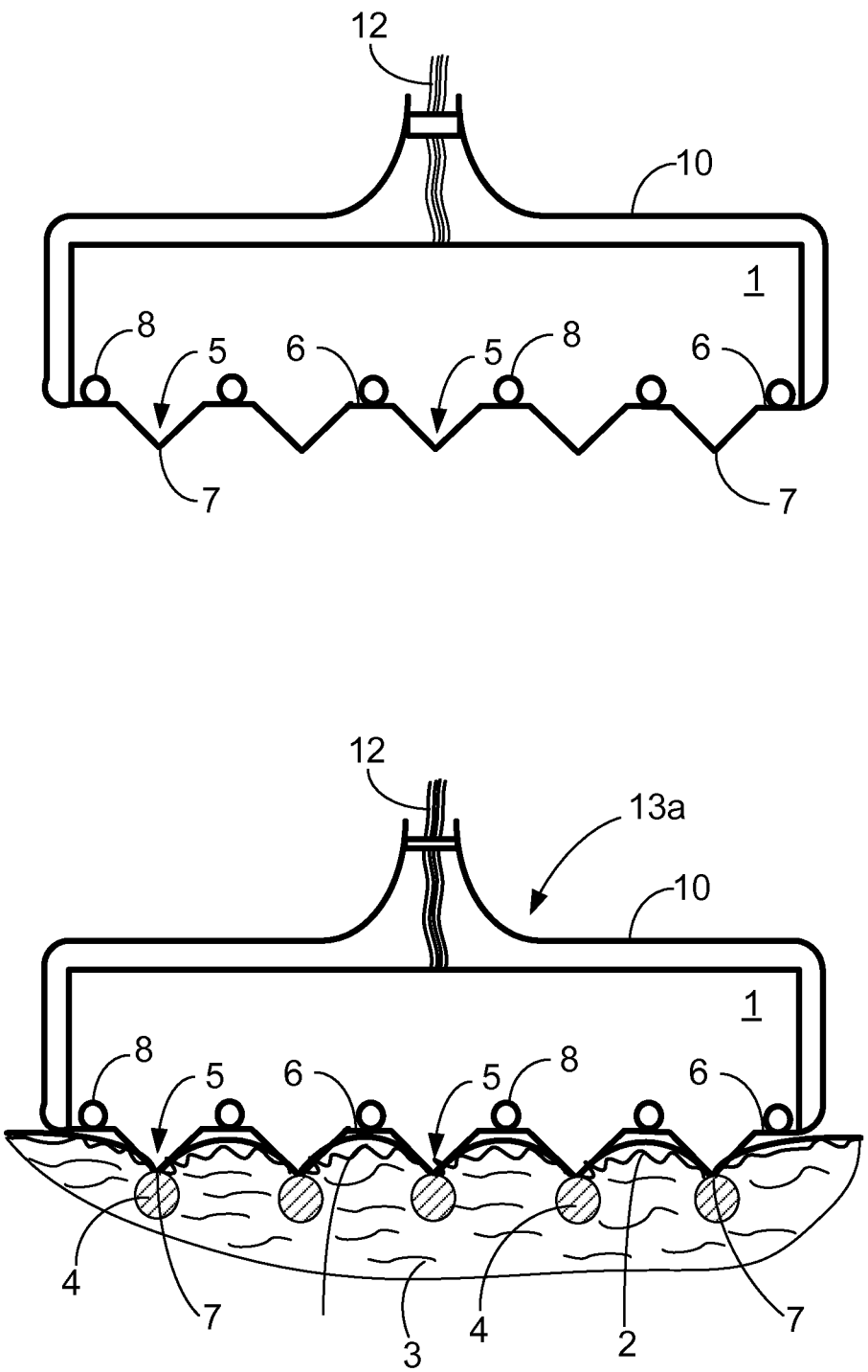
FIG. 2 shows an applicator for use in the system of FIG. 1.

FIG. 2 shows an applicator 13a that may be used for the applicator 13 in accordance with one embodiment of the invention. The applicator 13a comprises an electrode 1 from which a plurality of protruding conducting elements 5 extend. Each protruding element 5 (referred to herein as a "pin") terminates in a tip 7 having a high curvature. The electrical current from the tips is much higher than from flat parts 6 of the electrode. Skin volumes 4 around the tips 7 are therefore heated to a much higher temperature than the surrounding dermis 3 and epidermis 2, so that the skin volumes 4 may be heated to a coagulation temperature, while the skin temperature in the outside the volumes 4 are not heated to a coagulation temperature. The electrical energy is adjusted to selectively damage skin adjacent to tips so that the treatment of the skin occurs simultaneously at a plurality of discrete volumes 4. The pulse duration is preferably short enough to prevent significant heat diffusion far from the tips. In order to limit significant heat transfer from the tips, the pulse duration should preferably not exceed 200 ms. The selectivity of the treatment can be improved by electrode cooling of the skin surface. Cooling also causes a more uniform heat distribution at the tips. This can be achieved by circulating a cooling fluid through tubes 8 in the flat regions 6 between the pins 5. The electrode 1 is contained in a housing 10 connected to the cable 12. The cable 12 electrically connects the electrode 1 with a terminal of the power source 18. A second terminal of the power supply 18 may be connected to a ground electrode 20 via a cable 23 (See FIG. 1).

Figure 3:
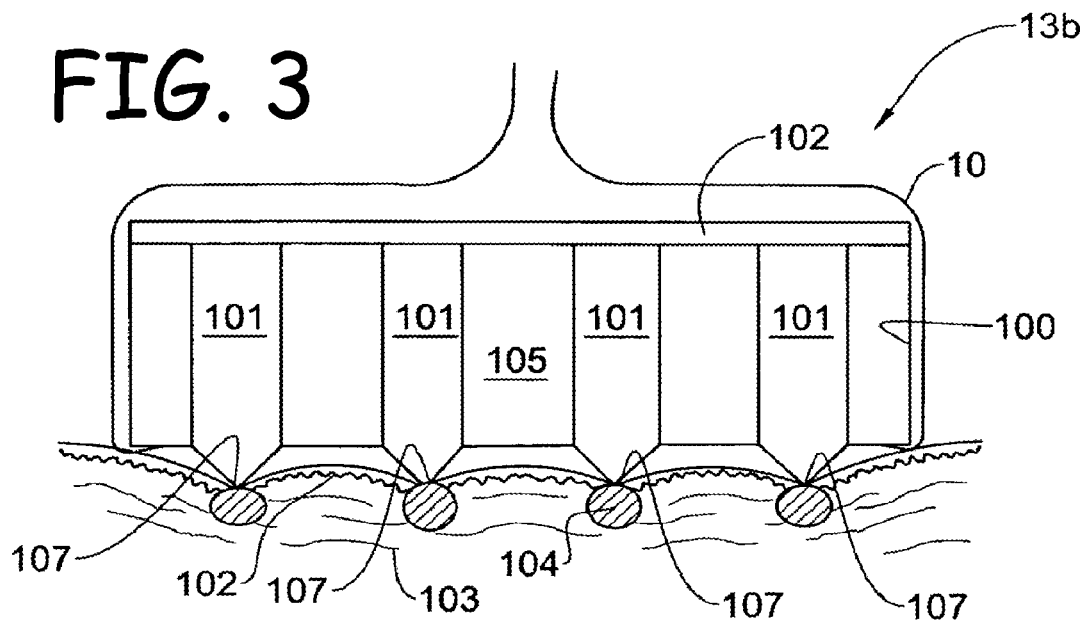
FIG. 3 shows a second applicator for use in the system of FIG. 1.

FIG. 3 shows an applicator 13b that may be used for the applicator 13 in accordance with another embodiment of the invention. The applicator 13b comprises an electrode 100 consisting of a plurality of conducting pins 101 extending from a conducting plate 102. The pins 101 are separated by electrical insulating material 105. The applicator 13b is used similarly as the applicator 13a to deliver electrical current to discrete volumes of skin 4.

The pins 5 in the applicator 13a and the pins 101 in the applicator 13b are provided with blunt tips 7 and 107, respectively. This prevents the pins 5 and 101 from penetrating into the skin when the electrode 13a or 13b is applied t the skin surface. Thus, the applicators 13a and 13b provide simultaneous non-invasive coagulation of skin regions 4.

Figure 4:
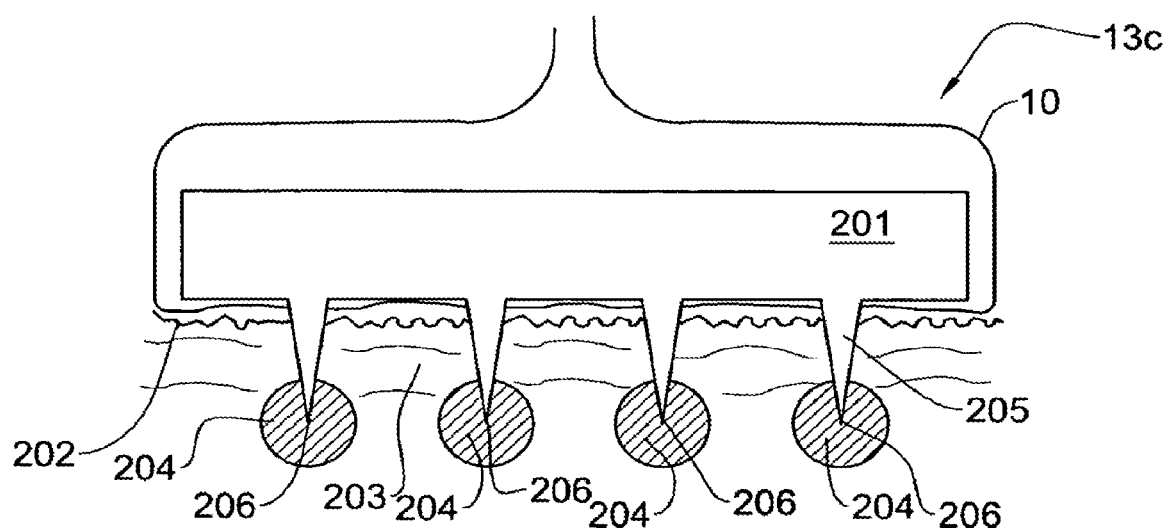
FIG. 4 shows a third applicator for use in the system of FIG. 1.

FIG. 4 shows an applicator 13c that may be used for the applicator 13 in accordance with another embodiment of the invention. The applicator 13c is configured to be used for invasive collagen remodeling. The applicator 13c includes an electrode 201 having a plurality of protruding conducting pins 205. The pins 205 have sharp tips 206 that are configured to penetrate through the epidermis 202 into the dermis 203 when pressed on the skin as shown in FIG. 4. The applicator 13c is used similarly to the applicators 13a and 13b so that the treatment of the skin occurs simultaneously in a plurality of discrete skin volumes 204. However, unlike the discrete volumes 4, which are located in the epidermis (see FIGS. 2 and 3), the volumes 204 are located below the surface in the dermis 203 (FIG. 4). This reduces skin redness that sometimes occurs when the treated regions are in the epidermis. A maximal current density is created at the tips of the pins 205. The sides of the protruding elements may be coated with insulating material to avoid skin heating around the pins 205 (not shown).

The present invention can be combined with other methods of skin treatment including laser treatment. For example non-ablative collagen remodeling by laser radiation may be combined with the invasive RF heating of the skin dermis in accordance with the invention.

The preferable parameters for non-invasive skin coagulation in accordance with the invention are as follows: Electrode size above 0.3 cm; Protruding element at contact with the skin up to 0.5 mm Protruding element height about 1 mm. Distance between protruding elements at least twice the element diameter; Current density: over 1 A/cm$^2$; RF current pulse duration: not longer than 0.5 sec; The optimal parameters for invasive skin coagulation: Electrode size above 0.3 cm; Pin diameter at contact with the skin not larger than 0.3 mm Pin protruding height above 1 mm. Distance between pins at least 1 mm; Current density above 0.1 A/cm$^2$; RF current pulse duration not longer than 0.5 sec.

What is claimed is:

1. A method for simultaneously heating a plurality of discrete skin volumes to a coagulation temperature, the method comprising:

applying an applicator to a skin surface, the applicator including at least one electrode having a plurality of spaced apart protruding conducting elements configured to contact the skin surface at a plurality of discrete locations, the conducting elements terminated by tips configured not to penetrate into the skin surface;

applying RF energy to the at least one electrode so as to generate an electrical current in the skin to simultaneously heat a plurality of discrete skin volumes to a coagulation temperature, wherein the conducting elements are spaced apart by a distance of at least 1 mm, and applying the applicator to the skin surface results in the conducting elements contacting the skin surface at spaced apart discrete locations.

2. The method of claim 1, further comprising cooling the skin surface when the conducting elements contact the skin surface.

3. The method of claim 2, wherein cooling the skin surface includes applying a pre-cooled fluid to the skin surface when the conducting elements contact the skin surface.

4. The method of claim 1, wherein applying RF energy to the electrode includes applying RF energy in pulses.

5. The method of claim 4, wherein the pulses have duration of less than 0.5 sec.

6. The method of claim 1, wherein applying RF energy to the electrode includes applying a current density of at least 1 A/cm2 at the tip.

7. The method of claim 1, further comprising separating the conducting elements from one another by an electrical insulating material disposed between the conducting elements.

8. A method for simultaneously heating a plurality of discrete skin volumes to a coagulation temperature, the method comprising:

applying a plurality of spaced apart conducting elements to a skin surface, the conducting elements configured to contact the skin surface at a plurality of discrete locations, the conducting elements terminated by end configured to be impenetrable to the skin surface;

applying RF energy to the conducting elements to generate an electrical current in the skin and simultaneously heat a plurality of discrete skin volumes to a coagulation temperature, wherein applying RF energy to the conducting elements includes applying RF energy sufficient to generate a current density of at least 1 Ampere/cm2 at the tips of the conducting elements.

9. The method of claim 8, further comprising cooling the skin surface when the conducting elements contact the skin surface.

10. The method of claim 9, wherein cooling the skin surface includes applying a pre-cooled fluid to the skin surface when the conducting elements contact the skin surface.

11. The method of claim 8, wherein applying RF energy to the electrode includes applying RF energy in pulses.

12. The method of claim 11, wherein the pulses have duration of less than 0.5 sec.

13. The method of claim 8, further comprising separating the conducting elements from one another by an electrical insulating material disposed between the conducting elements.

* * * * *